United States Patent
Chornenky et al.

(10) Patent No.: US 10,918,880 B2
(45) Date of Patent: Feb. 16, 2021

(54) METHODS AND APPARATUS FOR TREATMENT OF CHRONIC KIDNEY DISEASE

(71) Applicant: Minnesota Medical Physics LLC, Eden Prairie, MN (US)

(72) Inventors: Victor Ivan Chornenky, Minnetonka, MN (US); Ali Jaafar, Eden Prairie, MN (US)

(73) Assignee: Minnesota Medical Physics LLC, Eden Prairie, MN (US)

( * ) Notice: Subject to any disclaimer, the term of this patent is extended or adjusted under 35 U.S.C. 154(b) by 493 days.

(21) Appl. No.: 15/871,953

(22) Filed: Jan. 15, 2018

(65) Prior Publication Data

US 2018/0133498 A1 May 17, 2018

Related U.S. Application Data

(62) Division of application No. 14/822,577, filed on Aug. 10, 2015, now Pat. No. 9,884,199.

(Continued)

(51) Int. Cl.
*A61N 2/00* (2006.01)
*A61N 2/02* (2006.01)
(Continued)

(52) U.S. Cl.
CPC .............. *A61N 2/002* (2013.01); *A61F 7/007* (2013.01); *A61F 2007/0022* (2013.01);
(Continued)

(58) Field of Classification Search
CPC . A61N 2/002; A61N 1/40; A61N 2/02; A61N 2/004; A61F 7/007;
(Continued)

(56) References Cited

U.S. PATENT DOCUMENTS

| 6,424,864 B1* | 7/2002 | Matsuura | A61H 23/0245 607/3 |
| 2003/0158583 A1* | 8/2003 | Burnett | A61N 2/008 607/2 |

(Continued)

FOREIGN PATENT DOCUMENTS

RU 2103030 C1 * 1/1998

*Primary Examiner* — Kaylee R Wilson
(74) *Attorney, Agent, or Firm* — Skaar Ulbrich Macari, P.A.

(57) ABSTRACT

A method and apparatus for treatment of chronic kidney disease (CKD), particular diabetic nephropathy, are disclosed. The method comprises activation of adenosine A2a receptors in parenchymal and immune cells infiltrated into kidneys. The activation is performed by PEMF (pulsed electromagnetic field) stimulation applied locally to kidneys. Adenosine A2a signaling pathway is a potent anti-inflammatory and immuno-suppressive regulator that has been proven to attenuate inflammation and injury in diabetic nephropathy. Efficient activation of A2a receptors is achieved by applying electromagnetic field stimulation consecutively in 3 spatial dimensions. This allows attaining a significant increase in activation of A2a receptors in comparison with one-dimensional stimulation. Assistant thermal stimulation may be applied to increase expression of heat shock proteins (HSPs) in parenchymal cells. HSPs improve protein functions, protect cells from apoptosis and necrosis, increase metabolism, and symbiotically enhance effects of electric stimulation on CKD.

19 Claims, 8 Drawing Sheets

Related U.S. Application Data

(60) Provisional application No. 61/999,921, filed on Aug. 11, 2014.

(51) Int. Cl.
*A61F 7/00* (2006.01)
*A61N 1/40* (2006.01)

(52) U.S. Cl.
CPC .............. *A61F 2007/0071* (2013.01); *A61F 2007/0095* (2013.01); *A61N 1/40* (2013.01); *A61N 2/004* (2013.01); *A61N 2/02* (2013.01)

(58) Field of Classification Search
CPC ...... A61F 2007/0095; A61F 2007/0071; A61F 2007/0022
See application file for complete search history.

(56) References Cited

U.S. PATENT DOCUMENTS

| | | | |
|---|---|---|---|
| 2004/0098062 A1* | 5/2004 | Nachum | A61N 2/02 607/40 |
| 2011/0065976 A1* | 3/2011 | Chornenky | A61N 1/40 600/14 |

* cited by examiner

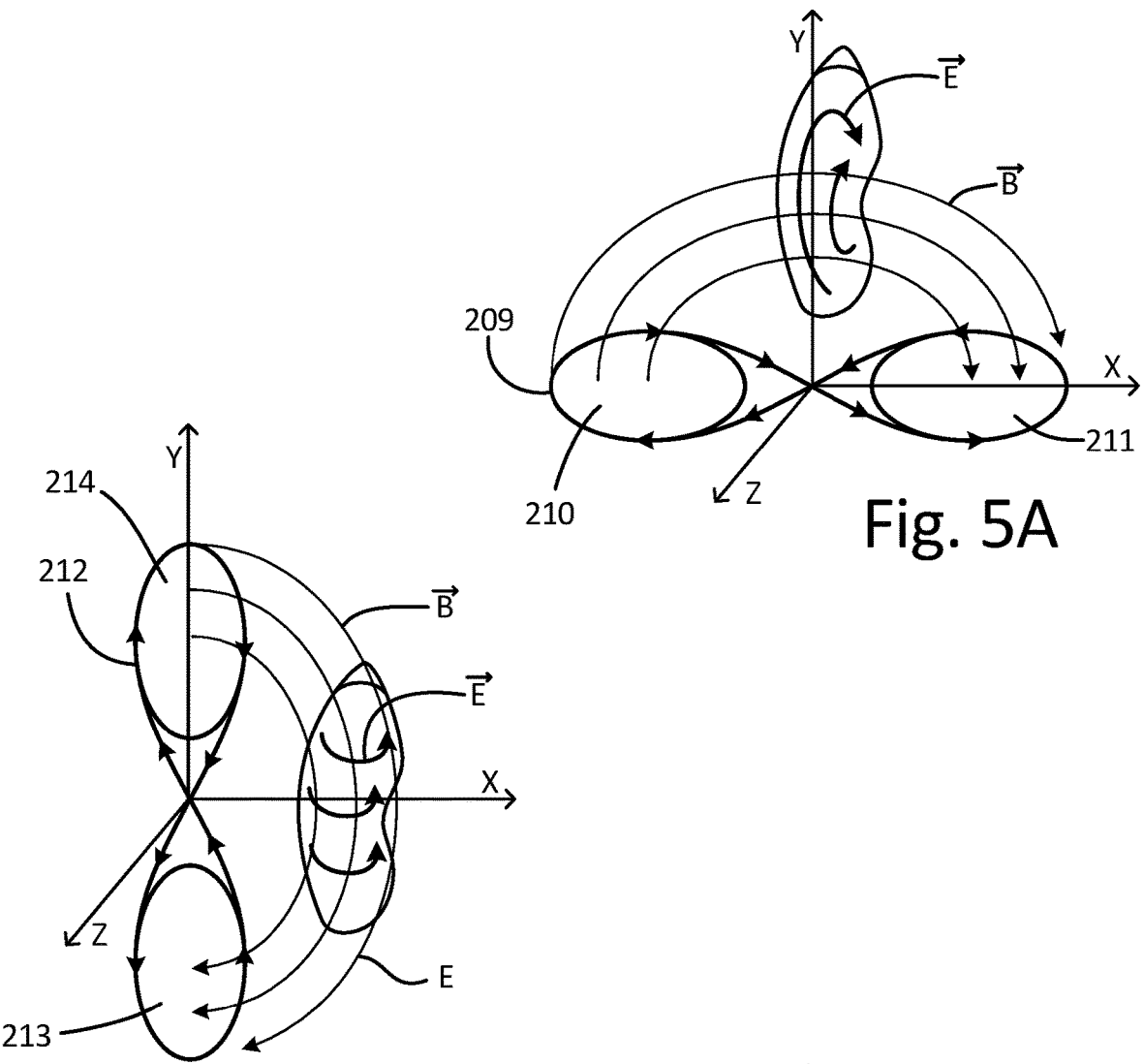
Fig. 5A
Fig. 5B
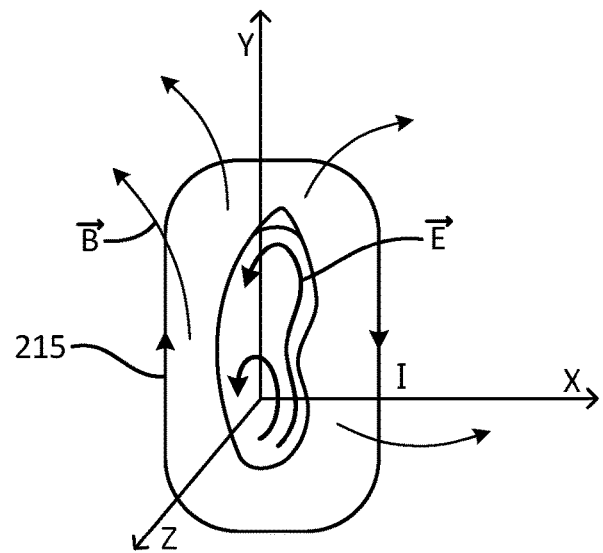
Fig. 5C

METHODS AND APPARATUS FOR TREATMENT OF CHRONIC KIDNEY DISEASE

PRIORITY

This application is a divisional of U.S. patent application Ser. No. 14/822,577, filed Aug. 10, 2015, which claims the priority benefit of U.S. Provisional Patent Application Ser. No. 61/999,921, filed Aug. 11, 2014, and both of which are hereby incorporated herein by reference in their entirety.

FIELD

The invention relates to treatment of kidney disease. More particularly, the invention relates to methods and apparatus for treating chronic kidney disease utilizing pulsed electromagnetic fields.

BACKGROUND

Kidneys are bean-shaped organs that serve as a biological filter removing metabolic waste from blood to the urinary bladder. The basic structural and functional unit of kidney is a nephron, the main function of which is to regulate the concentration of water and soluble substances in blood, reabsorbing the vital elements and excreting the rest as urine. In humans, a normal kidney contains 800,000 to 1.5 million nephrons. The adequate kidney function is imperative for survival: kidneys control level of electrolytes in blood, regulate blood volume, blood pressure and blood pH.

Bacterial infections, accumulation of toxic materials and auto-immune diseases may cause inflammatory disease of kidneys, also called nephritis. The symptoms of nephritis are a rise in blood pressure, back pain, edema and fatigue. Albumin and other serum proteins in increasing quantities pass into urine, creating a condition called proteinuria. If the condition continues to deteriorate, uremia or renal failure develops. Renal failure leads to accumulation of high concentrations of metabolic waste in the blood and eventually causes death. The conventional medical treatment is the removal of this waste by filtering blood with a dialysis machine, also called an artificial kidney. When the condition deteriorates still further, transplantation of a kidney is the last and the only option.

Chronic kidney disease has several underlying reasons and involves the glomeruli, tubules or interstitial tissue surrounding the glomeruli and tubules. The glomerulus is a network (tuft) of capillaries that performs the first step of blood filtration. The renal tubule is the part of nephron containing the fluid filtered through the glomerulus. Glomerulonephritis (GN) is inflammation of glomeruli. GN may lead to serious kidney damage and, in some patients, kidney failure. The causes of glomerulonephritis are complex and diverse, some have a genetic basis and others are associated with systemic diseases. While treatment is available for some types of GN, many traditional therapies are toxic, non-specific and have the potential for major side effects. Some GN subtypes do not respond to any therapies. Worldwide, GN is the most common single cause of end-stage renal disease (ESRD).

There are more than 20 million Americans with chronic kidney disease and 50,000 of them die annually.

Though chronic autoimmune disorders such as systemic lupus erythematosus affect a significant percentage of the human population and strongly diminish the quality of life and life expectancy, the molecular mechanisms of those diseases are still poorly understood, hindering the development of novel treatment strategies. Autoimmune diseases are caused by disturbed recognition of foreign and self-antigens, leading to the emergence of auto-reactive T-cells (so-called immunization phase). T-cells are a major regulator of the inflammatory cascade. The auto-reactive T-cells then trigger the second (so-called effector) phase of the disease which is characterized by activation of the immune cells that cause immune-mediated damage to host tissues.

For a long time, neutrophils have been neglected as potential players in the development of autoimmune diseases. However, a significant amount of new experimental data suggests that neutrophils play an important role in both the immunization and the effector phase of autoimmune diseases. Taken together, neutrophils should be considered as one of the most important cell types in autoimmune diseases and a suitable target for treatment of those diseases.

Neutrophils are the most common type of white blood cell in human body and are the first line of attack against invaders. In a person with a healthy immune system, the white blood cells gather at an infected or injured site in the body and produce chemical substances that help fight off the infection. These substances increase inflammatory reaction and attack invaders, causing some collateral injury to healthy tissue. Usually the immune system is capable of producing additional substances that make the inflammatory process self-contained and limited in time.

Inflammation in a healthy individual usually signals that the immune system is responding appropriately to harmful invaders, damaged cells, irritants, or injury. But, in case of autoimmune diseases, due to faulty interactions between blood and other immune system cells, the inflammation increases. Attracted by cytokines (messenger molecules) expressed by activated endothelium and other residential cells in inflamed tissues, neutrophils, using "roll", "stop" and "exit" mechanism leave blood vessels and congregate at a focus of infection. Migrated into the kidney, neutrophils release their own cytokines, which in turn activate several other cell types and amplify inflammatory response.

In addition to recruiting and activating other cells of the immune system, neutrophils play a key role in the front-line defense against invading pathogens. Neutrophils have three methods for directly attacking micro-organisms: phagocytosis, release of soluble anti-microbials substances, and generation of neutrophil extracellular traps (NETs). NETs are networks of extracellular fibers, primarily composed of DNA from neutrophils, which bind and kill extracellular pathogens while minimizing damage to the host cells. NETs may also have a deleterious effect on the host. It is believed that excessive expression of extracellular histone complexes from DNA combined with their slow clearing plays an important role in the development of autoimmune kidney diseases, particular in lupus.

There is a need in developing of novel therapies that inhibit recruitment of neutrophils from blood vessels and deactivate neutrophils that already aggregated in kidneys.

The autoimmune diseases cause significant numbers of patients that progress to ESRD. But the most important disease responsible for the highest number of patients with ESRD is diabetic nephropathy. The growing epidemic of obesity-related insulin resistance and the difficulties in managing diabetes have made diabetic nephropathy the major single cause of kidney disease in the developed world.

Despite current clinical interventions involving tight glycemic and blood pressure control, diabetic nephropathy progresses in most patients with a significant proportion reaching end-stage renal failure. In addition, the development of diabetic nephropathy exacerbates cardiovascular disease, which leads to increased morbidity and mortality. Given the limited renal protection with current treatments, it is critical that alternative therapeutic approaches are developed to protect diabetic patients from diabetic kidney disease.

Recent studies have identified macrophage-mediated injury as an important component in the development of diabetic nephropathy that is not addressed by current therapies. Further evidence has shown that macrophages are the major immune cells infiltrating the kidney in type 1 and type 2 diabetes, and that they contribute to the development of renal injury. In view of this new evidence, diabetic nephropathy has been reclassified as a chronic inflammatory disease which is triggered and maintained by metabolic disturbances of diabetes mellitus.

Elements of the diabetic milieu activate the vascular endothelium, inducing increased expression of cell adhesion molecules (ICAM-1/VCAM-1) that adhere to circulating blood monocytes. Using the "roll", "stop" and "exit" sequence the blood monocytes migrate from the blood vessels to the kidney, where they differentiate into macrophages. Glomerular podocytes, mesangial cells and tubular epithelial cells are also stimulated by the diabetic milieu. They additionally secrete chemokines (MCP-1/OPN) that facilitate transendothelial and intrarenal monocytes/macrophage migration. Also, the diabetic renal parenchymal cells produce colony stimulating factor-1 (CSF-1) which induces local proliferation of macrophages that also contributes to the accumulation of macrophages in diabetic kidneys.

Activated macrophages release reactive oxygen species and pro-inflammatory cytokines, which cause injury to podocytes, interstitial and tubular cells. These macrophages also can secrete profibrotic cytokines that induce mesangial and fibroblast proliferation and development of fibrosis. This ongoing renal injury and fibrosis promotes the progression of diabetic nephropathy.

Renal interstitial fibrosis (RIF) is the common pathological process of chronic kidney diseases leading inevitably to renal function deterioration. RIF and preceding epithelial-mesenchymal transition (EMT) are commonly triggered in diabetic kidney by an early occurring renal inflammation. However, an effective approach to prevent EMT and RIF is still lacking.

Adenosine A2a receptor recently emerged as a potent inflammation regulator. Adenosine activation of A2a receptors suppresses the EMT process and protects kidneys against RIF. Experimental studies suggest that activation of A2a significantly suppresses the deposition of collagen types I and III thus inhibiting the EMT progress. As a result, activation of A2a effectively alleviates EMT and RIF, suggesting A2a receptors as a potential therapeutic target for treatment of RIF.

Development of therapeutic strategies for treatment of macrophage-mediated injury in kidney that selectively target mechanisms of macrophage recruitment, proliferation and activation seems to be an attractive choice in comparison with general immunosuppression.

Now it is commonly accepted that macrophages play a critical role in the development of diabetic nephropathy. Current therapies, however, are unable to prevent the progressive renal damage caused by these inflammatory cells. There is an urgent need for novel anti-inflammation and immuno-suppressive therapies aimed at reducing macrophage recruitment, accumulation and activation in diabetic kidneys.

Adenosine is a purine nucleoside generated by metabolically stressed or inflamed tissues that is recognized as a major endogenous anti-inflammatory regulator. Under normal conditions, adenosine is continuously released from cells as a product of ATP degradation. Adenosine concentration in extracellular space is controlled by an enzyme called adenosine deaminase (ADA) which breaks it down and keeps the concentration level in low-micromolar to high-nanomolar range.

However, during conditions of stress, such as hypoxia during inflammation, levels of extracellular adenosine rise dramatically (up to 200-fold). This is partly due to increased production of AMP in hypoxic conditions, but substantial amounts of adenosine are also produced by the sequential dephosphorylation of adenine nucleotides released from platelets and hematopoietic cells, as well as damaged cells.

Adenosine regulates the function of the innate and adaptive immune systems through targeting virtually every cell type that is involved in orchestrating the immune/inflammatory response. Of the four adenosine receptors (A1, A2a, A1b, A3), A2a receptors have taken center stage as the primary anti-inflammatory effectors of extracellular adenosine. This broad, anti-inflammatory effect of A2a receptor activation is a result of the predominant expression of A2a receptors on monocytes/macrophages, dendritic cells, mast cells, neutrophils, endothelial cells, eosinophils, epithelial cells, as well as lymphocytes, NK cells, and NKT cells. A2a receptors play a critical role in controlling leukocyte trafficking by suppressing release of cytokines that induce production of adhesion molecules (ICAM-1/VCAM-1) and promote the "roll", "stop" and "exit" mechanism bringing neutrophils and monocytes/macrophages from blood vessels into tissues.

A2a receptor activation inhibits early and late events occurring during an immune response, which include immune cell trafficking, immune cell proliferation, proinflammatory cytokine production, and cytotoxicity. In late stage of inflammation in addition to limiting inflammation, A2a receptors participate in tissue remodeling and restoration. Consistent with their multifaceted, immunoregulatory action on immune cells, A2a receptors have been shown to impact the course of a wide spectrum of ischemic, autoimmune, infectious, and allergic diseases.

A2a receptors are found in all parenchymal cells in kidney: glomerular endothelium, podocytes, tubular endothelium and mesangial cells. Adenosine A2a receptor activation was recently shown to be renoprotective in diabetic nephropathy. Activated A2a receptors protect kidneys from diabetic nephropathy through actions on hematopoietic and kidney-derived cells. Podocytes contribute to the maintenance of the glomerular filtration barrier and abnormalities of podocyte structure and function lead to a number of glomerular diseases. Activation of adenosine A2a receptors preserves the structure and function of podocytes and leads to a reduction of proteinuria and preservation of glomerular function.

Macrophages play a critical role in immune response against pathogenic invaders. Beyond increasing inflammation and stimulating the immune system, macrophages also play an important anti-inflammatory role and can decrease immune reactions through the release of cytokines. Macrophages that encourage inflammation are called M1 macrophages, whereas those that decrease inflammation and encourage tissue repair are called M2 macrophages. This difference is reflected in their metabolism, where macrophages have the unique ability to metabolize one amino acid, arginine, to either a "killer" molecule (nitric oxide) or a "repair" molecule (ornithine).

Macrophages morph in phenotypes M1 or M2 depending on the environment in which they are activated. In the presence of cytokines such as IL-12 and IL-23 from T helper-1 cells that orchestrate initial stage of immune response, the "classically" activated macrophages are pro-inflammatory M1 type, whereas at the final stage of inflammation in presence of cytokine IL-10 and TGF-β from T helper-2 cells, macrophages become "alternatively" activated into anti-inflammation type M2, that promote tissue restoration. The same macrophage that was a pro-inflammatory M1 type at the beginning of inflammation can be re-activated into an anti-inflammatory M2 type at the final stage of the inflammation.

Consistent with its generally restorative function in tissues, A2a receptor activation has been repeatedly shown to have effects that prevent excessive classical macrophage activation thereby resulting in tissue protection. In contrast to the suppressive effect of adenosine on the production of proinflammatory mediators, adenosine augments production of anti-inflammatory cytokine IL-10 that promotes activation of macrophages into M2 type.

Thus, in addition to deactivating classically activated macrophages, A2a receptor signaling changes macrophage metabolism and enables switching their phenotype to alternative type M2 that participates in tissue restoration.

The protective effect of stimulation of A2a receptors was proven to correlate with decreased expression of adhesion molecules (ICAM-1/VCAM-1) and reduction of transmigration of neutrophil and monocytes/macrophages into the kidney. In addition, the renal microvasculature responds to A2a receptors stimulation by vasodilation that results in increased blood flow in the renal microcirculation and contributes to the renal protection.

Pulsed Electromagnetic Field Therapy (PEMF) is a new non-invasive method of treatment of numerous medical conditions related to injuries and inflammations of different tissues: bones, cartilages, soft and neurological tissues. For centuries it was a common knowledge that the natural wound healing involves generation of endogenous electric fields. Recently it has been discovered that the endogenous electric fields control also the processes of remodeling and healing bones and cartilages.

In PEMF therapy the electric field is carried into the treatment zone by a pulsed magnetic field produced by electromagnetic coils from outside the body. A PEMF system applies a series of magnetic pulses to injured tissue where each magnetic pulse induces an electrical signal that stimulates cellular anti-inflammatory and anabolic activities. PEMF therapy reduces pain associated with inflammation by suppressing production of pain mediator prostaglandin E2 and accelerates natural healing of tissues. Multiple studies have demonstrated effectiveness and safety of PEMF therapy in suppressing inflammation.

Recently it has been established by Varani et al. that the anti-inflammation mechanism of action of PEMF on a cell is due to its ability to increase the concentration of receptors A2a on the cell membrane. PEMF stimulation increases the number of active A2a receptors on the cell membrane by creating a conformational change of their protein and making them active and available for binding with adenosine ligand. The signal to the cell and the biological response of the cell's machinery depends on both the concentration of ligands in extracellular space and the concentration of receptors on the cell membrane. In other words, the magnitude of biological response of the cell depends on the product of these two concentrations. As a result, the same response can be achieved by two different ways: by changing concentration of adenosine around the cell or by changing concentration of the receptors on the cell membrane. The essence of the discovery of Varani et al. is that the adenosine signaling pathway can be up-regulated without changing extracellular adenosine concentration. It can be achieved by PEMF stimulation alone.

According to the experimental data, the A2a receptors can be up-regulated by the pulsed electric fields with amplitude above 50 μV/cm. In the environment rich in extracellular adenosine, which is always the case with inflamed or stressed tissues, the up-regulation of A2a receptors leads to significant amplification of adenosine signaling. PEMF stimulation triggers the same physiological response of the cell as an increase in concentration of adenosine or another A2a agonist in the extracellular space. In either case, the magnitude of signal from A2a receptors to the cellular machinery increases as well as the downstream effects of the A2a signaling.

PEMF stimulation can affect a wide variety of cells that express A2a receptors, including T cells, macrophages, neutrophils and other lymphocytes. All parenchymal kidney cells carry A2a receptors and can be stimulated by PEMF. A2a receptors stimulated by PEMF are able to inhibit multiple processes occurring during an immune response, including immune cell trafficking and proliferation, pro-inflammatory cytokine production and cytotoxicity. In addition to limiting inflammation, A2a receptors participate in tissue remodeling and repair. A2a receptors have been shown to impact the course of autoimmune, infectious, and allergic diseases.

PEMF stimulation of A2a receptors generates immuno-suppressive action by inhibiting overreactive immune cells, thereby protecting tissues from collateral inflammatory damage. PEMF stimulation of A2a receptors provides a novel regulatory tool for immune/inflammatory diseases of various organs, including kidney. They can be a critical part of the physiological negative feedback that limits local inflammatory responses. Increased by PEMF stimulation, A2a signaling inhibits development of cytotoxicity and cytokine-producing activity in T-cells. Stimulated by PEMF A2a receptors in autoreactive T-cells generate strong immunosuppressive action that reduces chronic inflammation and subsequent damage to the affected organ.

Upregulation of adenosine A2a signaling by PEMF in hematopoietic and renal parenchymal cells results in cascades of actions. It can down-regulate recruitment of inflammatory leucocytes from blood vessels by acting on the vascular epithelial cell and disrupting the "roll", "stop" and "exit" mechanism. Via A2a receptors signaling PEMF promotes changing phenotypes of macrophages from pro-inflammatory type M1 to anti-inflammatory type M2, stimulates resolution of inflammation and tissue restoration. It promotes improvement of function of podocytes, reduction of proteinuria, and down-regulation of expression of pro-inflammatory cytokines in mesangial cells—the major source of inflammation in diabetic kidney. Also it inhibits renal interstitial fibrosis (RIF) by suppressing the epithelial-mesenchymal transition (EMT).

These outstanding anti-inflammation and immuno-suppressive actions of A2a receptors attracted attention of many researchers as a potential basis for development of new drugs for treatment of various inflammatory diseases. Unfortunately, free adenosine has a very short half-life time in plasma, about 10 seconds, which severely limits its usage as a systemic drug. However, a number of agonists with high selectivity to A2a receptors and long half-life in plasma have been developed recently, keeping the hope of developing these drugs alive.

It should be noticed that all new knowledge recently accumulated about A2a effects on the inflamed tissues came mainly from in vitro experiments and animal trials. Unfortunately, in human clinical trials, a big problem with adenosine agonists has been encountered—a strong hemodynamic effect.

A2a receptors are abundantly expressed in vascular endothelium and play a significant role in regulating blood flow throughout the body. Systemic activation of A2a receptors leads to vasodilation in the whole vascular bed and increases blood flow, which, in turn, creates a significant reactive drop in blood pressure, increase in heart rate and cardiac index. These hemodynamic side effects limit systemic dosing of A2a agonists to the level at which they are no longer effective at resolution of inflammation. This problem has contributed to the failure of several A2a agonists. Examples of discontinued A2a agonists trials include GW328267X from GlaxoSmithKline PLC and UK-432097 from Pfizer Inc. Several A2a agonists, though, are still in clinical trials for inflammation-related indications.

The anti-inflammation and immuno-suppressive actions of A2a receptors can be employed by using PEMF stimulation of the affected areas. For more than thirty years of experimental and clinical use of PEMF stimulation for different tissues there were no noticed side effects. PEMF stimulation boosts activity of A2a receptors locally; it does not increase the concentration of adenosine around the cells, but instead, increases A2a concentration on the cellular membranes.

Local PEMF stimulation effects inflamed tissues only, where the concentration of adenosine is high, up to 200-fold of the base line. As has been mentioned before, under normal physiological conditions concentration of adenosine in tissues is low and PEMF stimulation effects are minimal. This is the major reason why PEMF therapy does not have side effects.

Stress response is one of the most important biological reactions to a wide variety of unfavorable physiological and environmental conditions. It is a part of cell's own repair system that is evolutionary conserved and universally expressed from bacteria to humans. One of the first cellular reactions on stress is rapid generation of so called heat shock proteins (HSPs). Heat-shock proteins play numerous roles in cell function, including modulating protein activity by changing protein conformation, promoting multi-protein complex assembly/disassembly, regulating protein degradation within the proteasome pathway, facilitating protein translocation across organelle membranes, and ensuring proper folding of nascent polypeptide chains during protein translation.

When cells are overstressed, the common response is to undergo cell death by one of two pathways, either 'necrosis' or 'apoptosis'. Recently, both routes to cell death have been revealed to share similar mechanisms, with heat shock proteins and their cofactors responsible for inhibiting both apoptotic and necrotic pathways. So, the effective biological function of HSPs is to preserve cell survival by maintaining the vital functions of proteins.

In practical terms, HSPs can be induced by local thermal stimulation with temperatures 40-43 degrees C. for 10-30 minutes.

Deep thermal stimulation can be achieved by ultrasound, high radiofrequency and microwave diathermia devices. Also, kidneys can be stimulated as a part of the whole body thermal stimulation in a hot bath, sauna and steam room.

After thermal stimulation, intracellular concentration of HSPs rapidly grows to several fold level at 24 hours and returns to the basal level after 48-72 hours. Intracellular buildup of HSPs is triggered by activation of Heat Shock Factor (HSF), whereas HSP concentration is controlled by enzyme adenosine deaminase (ADA) that degrades HSPs. Luckily, the activity of ADA is inhibited by PEMF stimulation, so, as a result, PEMF helps to keep the HSPs concentration high.

It is known from animal studies that HSP72 inhibits proliferation and apoptosis in tubular cells and diminishes accumulation of fibroblasts and collagen in renal parenchyma, thus slowing the process of fibrosis. It was also observed that HSP70 exerts strong cytoprotection of mesangial cells from oxidative injury in experiments with ischemic reperfusion. Overall, a significant body of evidence suggests that HSPs delay the progression of chronic kidney disease (CKD) by the anti-apoptotic activity and cytoprotection.

Koga et al. in the article "Mild electrical stimulation and heat shock ameliorates progressive proteinuria and renal inflammation in mouse model of Alport syndrome" demonstrated that combination of electrical and heat stimulation provides anti-proteinuric and anti-inflammatory effects on Alport mice through multiple signaling pathways via podocytic activation of Akt (protein kinase B) and induction of HSP72. The authors suggest a new therapeutic strategy to decelerate the progression of Alport syndrome by applying combined electrical and heat stimulation. In the experiment described in the article, the electrical stimulation was provided by a pulsed direct electric current applied to the experimental animals via electrodes attached to the skin. The thermal stimulation was delivered from the same electrodes.

In U.S. Pat. No. 6,941,172 B2, issued to Zvi Nachum, a "Method and device for restoring kidney function using electromagnetic stimulation" is disclosed. The method of restoring kidney function includes the steps of: (a) providing a device including: a conducting coil, and a signal generator for providing a plurality of electrical impulses to the coil; (b) disposing the conducting coil proximate to a kidney of a patient, and (c) delivering the electrical impulses conducted to the conducting coil, so as to produce an electromagnetic field, the electromagnetic field acting so as to stimulate the kidney. The inventor states that this method is applicable only to the cases of acute kidney failure, mainly for traumatic ones, not to CKD: "The device and method of the present invention appear to be most effective in treating kidney failure due to trauma.

Kidney failure due to trauma is acute, and is generally reversible, at least during the initial stages. Without wishing to be limited by theory, it is believed that a static charge builds up within the tissues of the kidney, for reasons that are not yet fully understood. This static charge inhibits proper functioning of the kidney. As long as no significant irreversible damage has been caused to the kidney, the kidney can be stimulated into regaining normal performance by clearing the static charge within the tissues of the kidney by application of an electromagnetic field using the device and method of the present invention".

It should be mentioned that it is widely accepted in the art that the biologically active component of electromagnetic stimulation is the electric field produced by the changing magnetic field. In the Nachum patent mentioned above, there is no disclosure of the magnitude of the electric field applied to the kidney. But from the time dependency of the magnetic field which is described in the patent, it can be easy estimated that the electric field was about 1 µV/cm or less. This level of electric field is, probably, enough to change the pathologic charging in the kidney caused by trauma, but it is not enough to up-regulate the A2a receptors on kidney cells. In other words, the disclosed Nachum method, developed for restoration of kidney function of a traumatized kidney, cannot be effective in preservation of kidney function deteriorating due to chronic inflammation of kidney. In particular, Nachum makes an explicit "distinction between acute and chronic renal failure is of cardinal importance" as explained in Column 1 starting at line 19 of his patent. Chronic kidney disease and acute renal failure are clearly two different diseases.

Therefore, there continues to be a need for devices and methods for treating chronic kidney diseases.

SUMMARY

The present invention effectively addresses certain drawbacks in the prior art kidney disease treatment devices and methods. One object of certain embodiments is to provide PEMF stimulation for reduction of kidney inflammation and suppression of excessive immune response. Another objective of certain embodiments is reduction of proteinuria, deceleration of progression of chronic kidney disease and preservation of kidney function. Another objective of certain embodiments is to treat autoimmune diseases of kidneys. Yet another objective of certain embodiments is to treat diabetic nephropathy. Another objective of certain embodiments is to apply highly efficient PEMF stimulation to activate A2a receptors of parenchymal kidney cells and the immune cells accumulated in kidneys: T-cells, macrophages and neutrophils. An objective of certain embodiments is to provide thermal stimulation to kidneys to increase vitality of kidney cells by induction of Heat Shock Proteins including HSP72 that inhibit apoptosis and necrosis of kidney cells. Another objective of certain embodiments is to provide for treatment of kidneys a portable self-administered system that combines PEMF with thermal stimulations, which does not interfere with everyday activity and that can be used in office, home or in a car.

The aforementioned objectives can be achieved by providing a Thermally Assisted Pulse Electromagnetic Field (TA-PEMF) stimulation system that delivers both thermal and electric stimulation to kidneys. The thermal stimulation is delivered by heating elements made of carbon fiber (CF) fabric secured to a belt that placed on the patient's back adjacent to kidneys. The electric stimulation with enhanced efficiency is provided by three PEMF coils on each kidney, one is made as a flat spiral coil (Tesla coil) and two others are shaped in number 8 shape, one horizontal and one vertical. Three coils and the heating element comprise a stimulation element that is secured to the belt adjacent to kidney. The heating elements, controlled independently from PEMF coils, provide temperature at the surface of the body in the range of 40-43 degree C. that induces HSPs in kidneys. The electrical stimulation, generated by PEMF coils, delivers rectangular electric pulses to kidneys with amplitudes, durations and frequencies that activate A2a receptors on both kidney-derived and immune cells.

The disclosure includes a method and apparatus for treatment of chronic kidney disease (CKD), particular diabetic nephropathy. The method can include activation of adenosine A2a receptors in parenchymal and immune cells infiltrated into kidneys. The activation is performed by PEMF (pulsed electromagnetic field) stimulation applied locally to kidneys. Adenosine A2a signaling pathway is a potent anti-inflammatory and immuno-suppressive regulator that has been proven to attenuate inflammation and injury in diabetic nephropathy. Efficient activation of A2a receptors is achieved by applying electromagnetic field stimulation consecutively in 3 spatial dimensions. This allows attaining a significant increase in activation of A2a receptors in comparison with one-dimensional stimulation. Assistant thermal stimulation may be applied to increase expression of heat shock proteins (HSPs) in parenchymal cells. HSPs improve protein functions, protect cells from apoptosis and necrosis, increase metabolism, and symbiotically enhance effects of electric stimulation on CKD.

The disclosure includes a pulsed electromagnetic field therapy stimulation system for delivering treatment to a patient with chronic kidney disease. The system includes an applicator and a first stimulation unit disposed in the applicator and located such that the first stimulation unit is disposed over a first kidney of the patient when the applicator is worn by the patient. The first stimulation unit comprises a plurality of coils. A first coil comprises a first petal and a second petal, the second petal extending longitudinally opposite the first petal along a first longitudinal axis, and defining a first coil crossover point where the first and second petals intersect. A second coil comprises a first petal and a second petal, the second petal extending longitudinally opposite the first petal along a second longitudinal axis, and defining a second coil crossover point where the first and second petals intersect. A third coil comprises a perimeter loop. The first coil, second coil and third coil are disposed in a plane. The first longitudinal axis is axially rotated ninety degrees with respect to the second longitudinal axis. The first coil crossover point and second coil crossover point coincide. The first coil and the second coil are disposed within the perimeter loop of the third coil.

The disclosure further includes a pulsed electromagnetic field therapy stimulator for treatment of chronic kidney disease in a patient. The stimulator is coupled to a controller and a power source. The controller is configured to selectively generate an electrical current to one or more coils. The stimulator includes a first coil oriented along a first orthogonal axis. The first coil comprises a first petal and a second petal. The second petal extends longitudinally opposite the first petal such that an electrical current in the first petal flows in a first rotational direction and the electrical current in the second petal flows in a second rotational direction, wherein the second direction being opposite of the first direction. The stimulator also includes a second coil oriented along a second orthogonal axis ninety degrees offset from the first orthogonal axis. The second coil comprises a first petal and a second petal. The second petal extends longitudinally opposite the first petal such that an electrical current in the first petal flows in a first rotational direction and the electrical current in the second petal flows in a second rotational direction, wherein the second direction being opposite of the first direction. The first orthogonal axis and the second orthogonal axis lie in a common plane. A third coil can also be provided. The third coil comprises a loop disposed in the common plane and surrounds the first coil and the second coil.

The disclosure additionally includes a method of treating chronic kidney disease of a mammal. The method includes increasing a concentration of Ata adenosine receptors on cellular membranes in a kidney of the mammal by delivering a first pulsed magnetic field with a first polarity to the kidney of the mammal along a first orthogonal direction. A second pulsed magnetic field with the first polarity is delivered to the kidney of the mammal along a second orthogonal direction. The second orthogonal direction is perpendicular to the first orthogonal direction. The first and second orthogonal directions are also in a common plane. A third pulsed magnetic field with the first polarity is further delivered to the kidney of the mammal along a third orthogonal direction. The third orthogonal direction is perpendicular to the common plane.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIGS. 5*a*, 5*b* and 5*c* are diagrams of PEMF stimulation of kidney according to an example embodiment.

Figure 1:
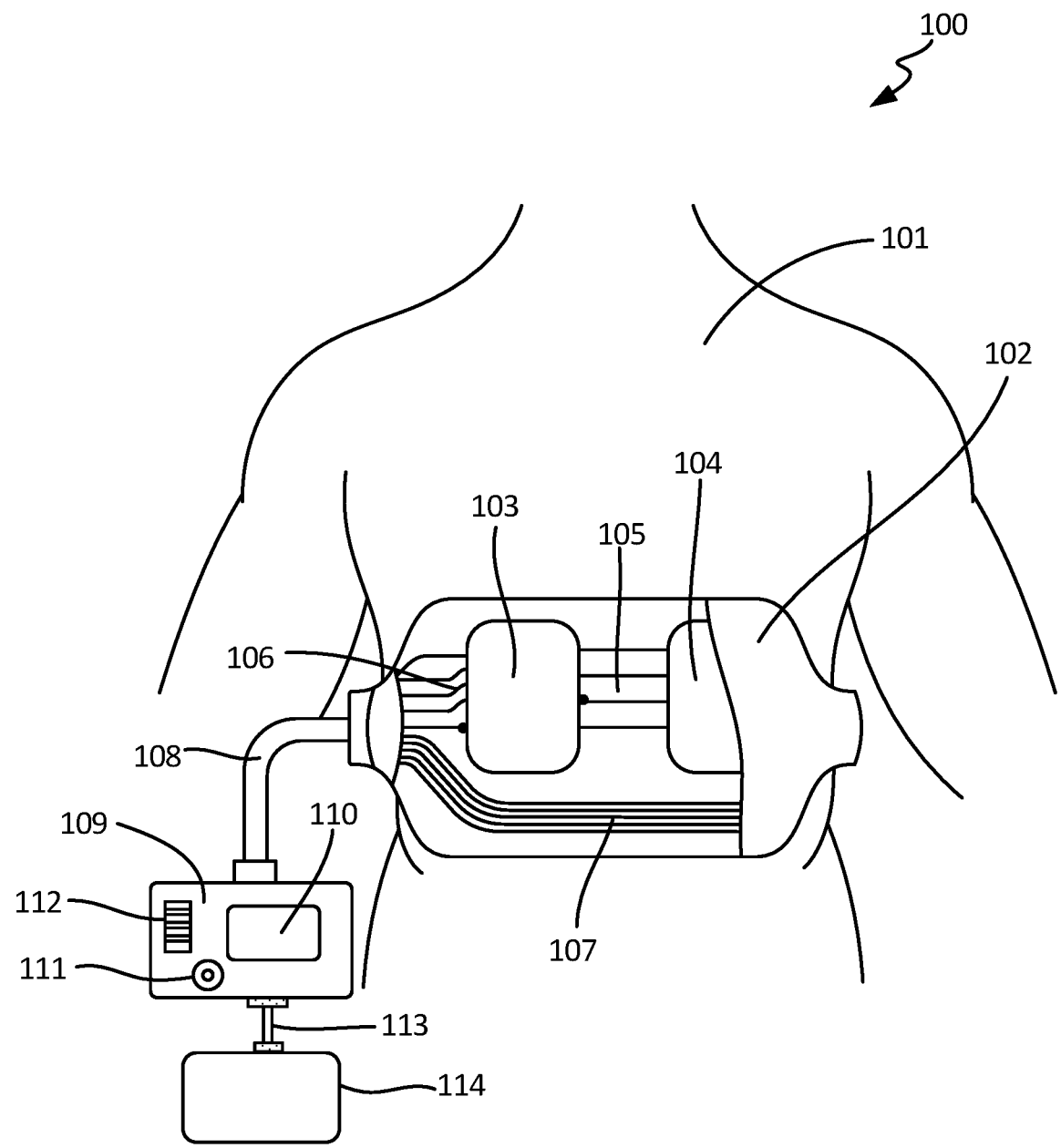
FIG. 1 is a PEMF system for treatment of a kidney according to an example embodiment.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

An embodiment of a method and apparatus for treatment of chronic kidney disease is illustrated by FIG. 1. The TA-PEMF stimulation system 100 for treatment of chronic kidney disease is shown with reference to the back 101 side of the patient. An applicator 102 such as a belt attachable to the back of the patient is secured adjacent to the patient and arranged such that a first TA-PEMF stimulation unit 103 is disposed over the left kidney and a second TA-PEMF stimulation unit 104 is disposed over the right kidney.

Electrical conduits 105 connect the first and second TA-PEMF stimulation units. The stimulation units 103, 104 can be connected in series, as shown in FIG. 1, or in parallel to each other.

Additional electrical conduits 106 and 107 connect both stimulating units 103 and 104 to conduit 108 and further to a controller 109.

The controller 109 is a computerized control unit, including both a processor and memory, to control the power and operation of the stimulation units disposed in the applicator 102. The controller 109 further includes a display 110, and on/off control button 111 and temperature indicator 112 (e.g. a bar indicator, digital numerical display, sequential LEDs or other similar indication means). Rotation of button 111 allows user to select a desired level of treatment temperature within permissible boundaries.

A power cable 113 or conduit connects controller 109 to power supply 114, which can be a battery or DC power supply connected to an AC power outlet. The power supply can also be combined with controller into a single integrated housing.

Figure 2:
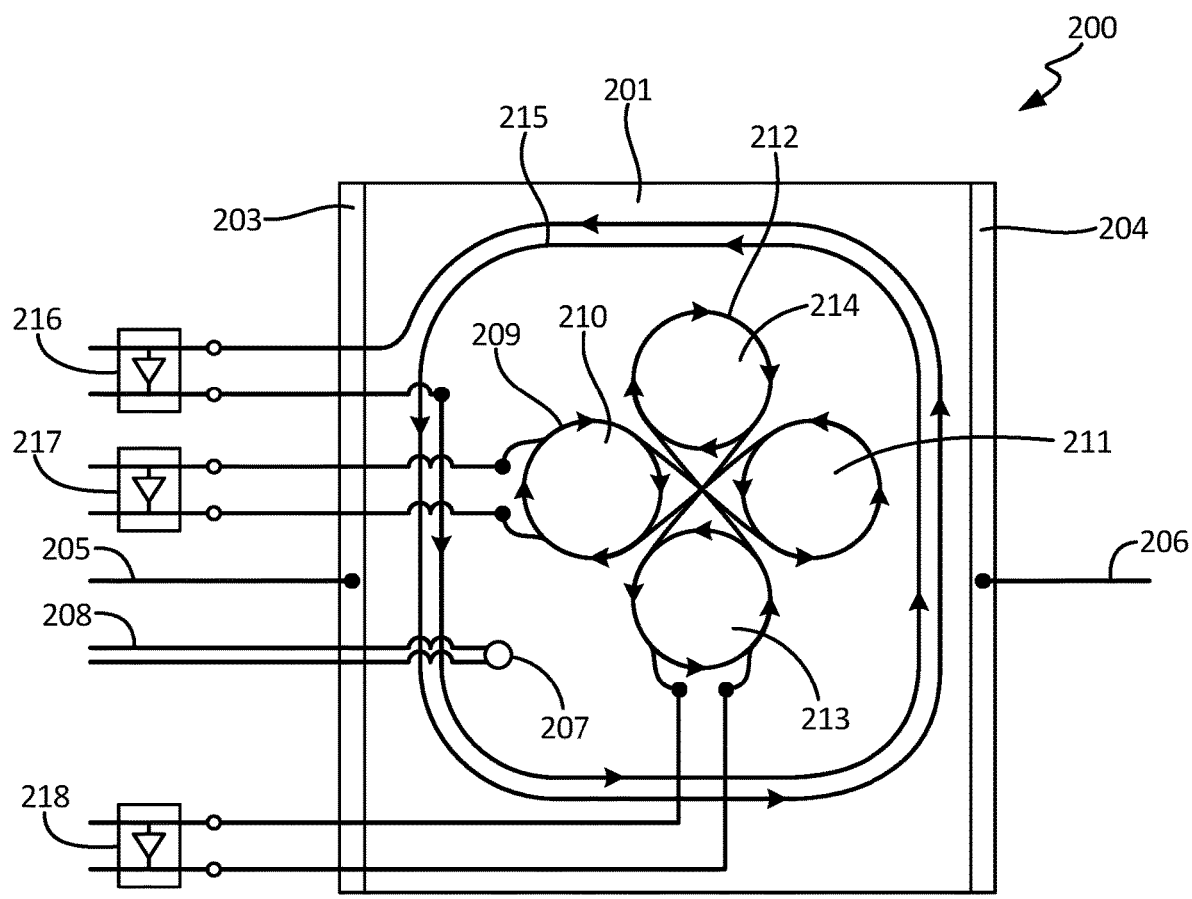
FIG. 2 is a schematic of a TA-PEMF stimulation unit according to an example embodiment.

FIG. 2 schematically depicts a TA-PEMF stimulation unit 200. A flat resistive heater 201 made of flexible carbon fiber fabric (CF) is provided. Conductive electrodes 203 and 204 are connected to the resistive CF heater 201 and to controller 109 by respective wires 205 and 206. A thermal sensor 207 is secured on heater 201 and is functionally connected to controller 109 by a pair of wires 208.

Controller 109 provides DC pulsed power to heater 201. These pulses can be short, long, with modulated duration, or can be trains of short pulses with modulated numbers of pulses. The presence, duration and number of these pulses depends on the readings of thermal sensor 207 and the treatment temperature selected by user.

Controller 109 is programmed with a software code to modulate the pulse durations or their number and is programmed to stabilize the temperature of heater 201 at a user-selected level.

Figure 8:
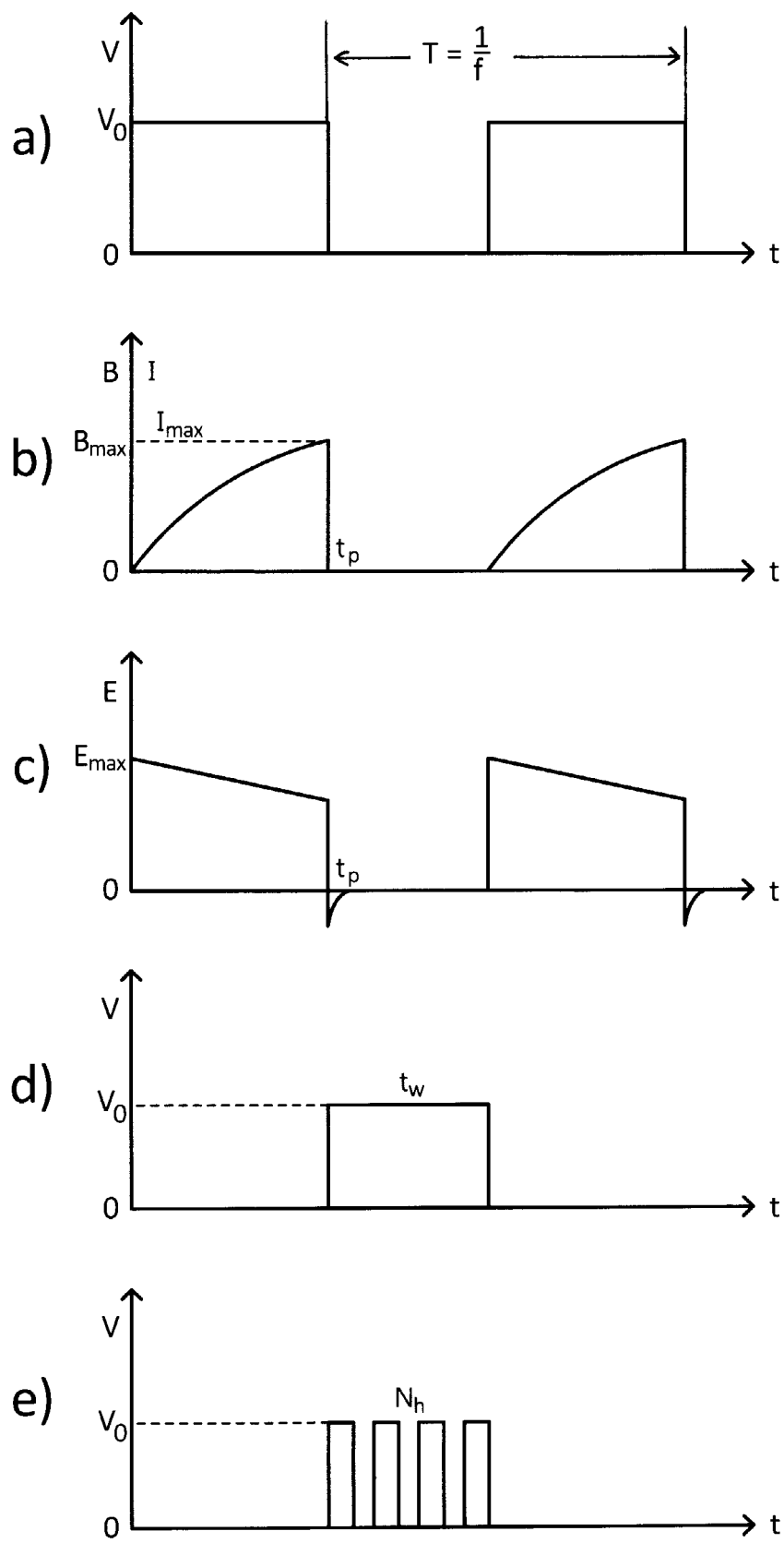
FIG. 8 is a series of diagrams illustrating voltage (a), current and magnetic field (b), electric field (c) and thermal pulses (d and e) used in a PEMP stimulation apparatus according to an example embodiment.

A horizontal figure 8-shaped coil 209 with two petals 210 and 211, which can be performed as two round coils connected to each other with opposite polarities, a vertical figure 8-shaped coil 212 with two petals 213 and 214 similar to petals 210 and 211, and an oval shaped coil 215 are each provided to the stimulation unit 200 to provide sequences of electromagnetic pulses in the treatment target area.

Petals 210 and 211 of the horizontal coil 209 carry electric currents in opposite directions—clockwise and counterclockwise and deliver axial magnetic fields to the treatment area in opposite directions: in the body and out of the body.

At the target area in kidney, which is about 5 cm displaced from the plane containing each of the coils, the axial components generated by two coils mutually compensate each other, so the axial magnetic field in the target area is close to zero. At the same time, the radial components of the magnetic fields created by petals 210 and 211 are of the same direction and add up, creating a substantial magnetic field along the horizontal axis parallel to the plane of coils.

Likewise, petals 213 and 214 of the vertical coil 212 deliver magnetic field along a vertical axis parallel to the plane of coils.

Coil 215 delivers axial magnetic field in the direction normal to the plane of coils.

The system of three coils 209, 212 and 215 are, therefore, able to provide sequential pulsed magnetic fields along all three spatial directions X, Y, Z. Note that the system of three coils can be rotated from the depicted orientation, while maintaining their respective orientations with one another, without departing from the scope of the invention.

For protection of electronic controller and the coils 209, 212 and 215 from high voltage spikes arising at the end of electromagnetic pulses, all three coils are connected in parallel with free wheel diodes 216, 217 and 218. These free wheel diodes can be secured on the belt applicator 102 or can be a part of the controller 109 or contained within the controller housing.

All coils and the heater are held together by flexible glue, preferably silicone RTV rubber, not shown.

Figure 3A:
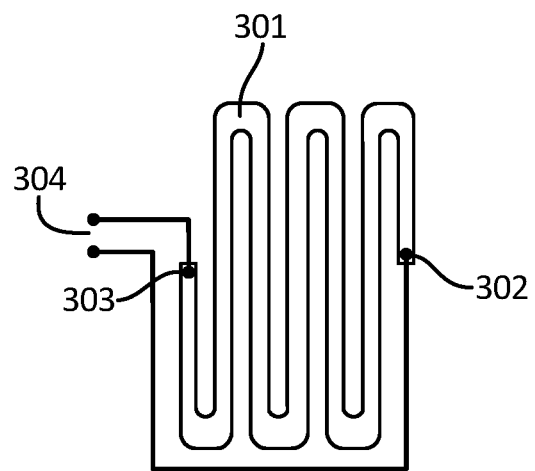
FIG. 3*a* is a schematic of a heater for a TA-PEMF stimulation unit according to an example embodiment.
Figure 3B:
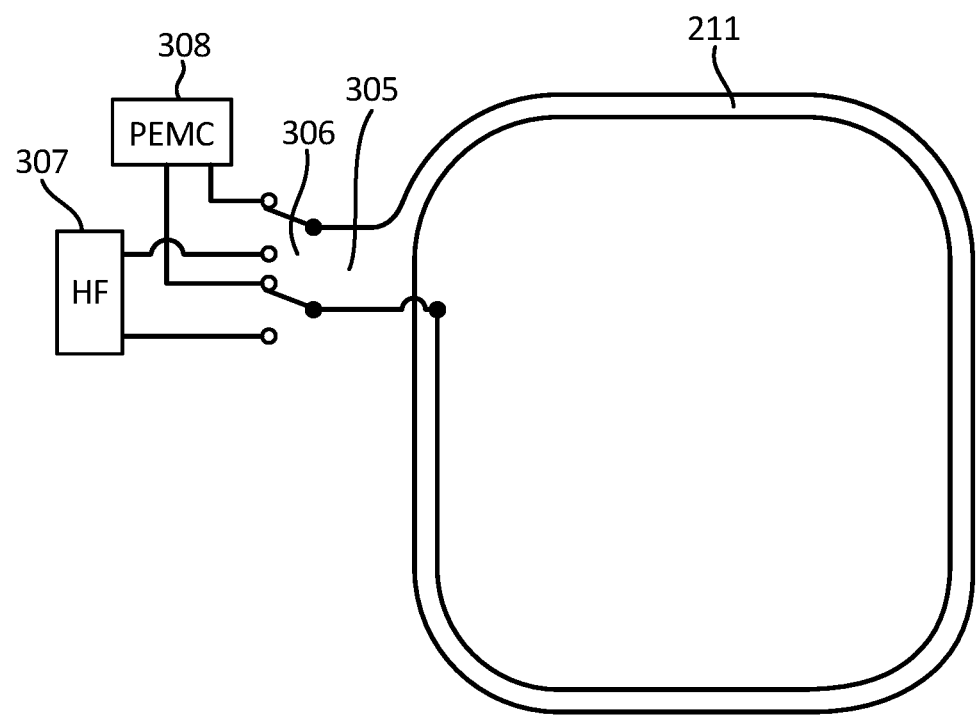
FIG. 3*b* is a schematic of another heater for a TA-PEMF stimulation unit according to an example embodiment.

Certain alternative heaters configurations that can be used in TA-PEMF stimulation unit 200 are shown in FIGS. 3a and 3b. In FIG. 3a, the carbon fiber heater is made of a meandering CF strip 301 attached to the belt applicator (not shown). The ends of the CF strip 302 and 303 are connected to the power output of controller 209 to supply the power necessary for heating. This heater comprises a long CF strip, so it has a higher resistance than heater 201, consumes less current and can be used for delivering long pulses.

FIG. 3b shows an inductive heater 305 powered by a high frequency generator. The inductive heater 305 can be used for deep heating of kidneys and comprises a coil, which can be independent or be one of PEMF coils (e.g. coil 211). In this embodiment, the controller 109 via a switch 306 intermittently connects coil 211 to high frequency generator 307, thus providing deep heating of the target area or to PEMF circuit delivering electromagnetic stimulation. Based on readings of the thermal sensor on the belt applicator and the treatment temperature selected by the user, the controller 109 selectively controls the power outputs to provide stabilization of temperature at a desired level.

Figure 4:
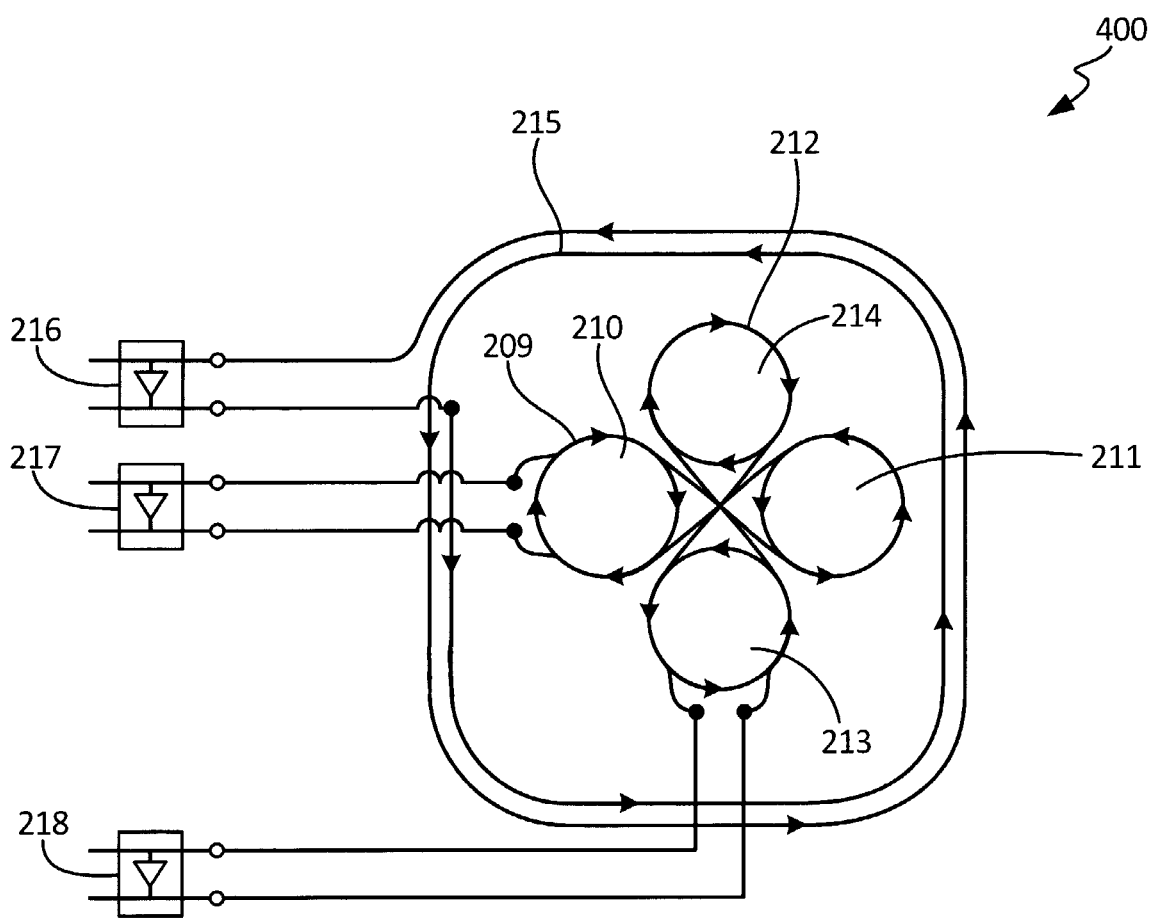
FIG. 4 is a schematic of a stimulation unit according to an example embodiment.

FIG. 4 shows another implementation of the stimulating unit for treatment of CKD, which employs only a set of PEMF stimulation coils and does not include a heater. This embodiment of the apparatus consumes significantly less energy than the previous embodiments. The tradeoff is between a long treatment and a short treatment accelerated by heat stimulation. With average consumption of energy under 10 Watts and lithium batteries, this embodiment of the treatment device can work for several hours without recharging and can provide effective and efficient treatment.

In addition, thermal stimulation can be provided by independent devices for deep heating, like ultrasound or high frequency diathermia devices. Or, induction of heat shock proteins (HSP) in a kidney can be achieved by the whole body thermal stimulation in a bathtub, sauna or steam room. Three 10-30 minute sessions a week allows maintaining an elevated concentration of HSPs in kidneys.

PEMF and heat stimulation can be separated in time and still be efficient and efficacious. Even without heat stimulation, the disclosed method of treatment of CKD can be successfully employed for treatment of CKD using long (3-4 hours) daily treatment sessions. A portable, battery powered PEMF device with "daisy" resembling coils in the stimulator makes this strategy easy and efficient.

The process of PEMF stimulation of kidney is schematically illustrated in FIGS. 5a, 5b and 5c, wherein coils, kidney, magnetic and electric fields are depicted in a rectangular system of coordinates XYZ. Three coils, such as previously described, are sequentially energized by the controller. The directions of respective electrical currents are shown in FIGS. 5a-5c by arrows.

Coil 209 with two horizontal petals 210 and 211 delivers a pulsed magnetic field B, lines of which are parallel to the ZX plane and normal to Y axis. This magnetic field induces electric field E, lines of which are parallel to the YZ plane and normal to X axis. The electric field E lines are locked on themselves and are induced in the whole area around the coils, including the kidney and surrounding tissues. For simplicity in FIGS. 5a-5c, they are shown only in the kidney. Coils 212 and 215 deliver electric field E in planes normal to the Y and Z axes, correspondingly.

The disclosed system of electromagnetic coils is positioned in one plane but is configured to deliver three-dimensional electromagnetic stimulation (3-D PEMF). This novel arrangement of electromagnetic coils generally resembles a flower, such as a daisy. The "daisy" stimulator provides every cell in a treatment zone with sequential stimulation by electric fields in each of the three directions: Ex, Ey and Ez.

Figure 6A:
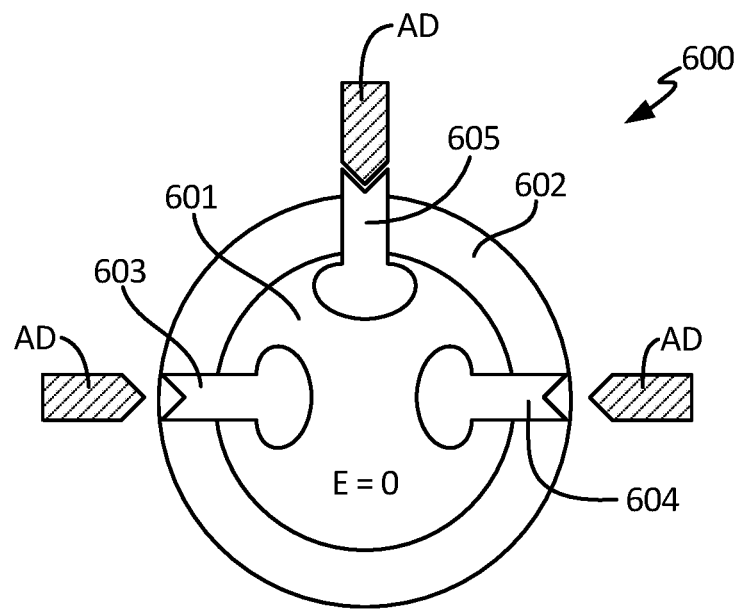
FIG. 6*a* is a diagram of the interaction of adenosine receptors with the electric field due to PEMF stimulation of the kidney according to an example embodiment where the cell is shown without electric field.
Figure 6B:
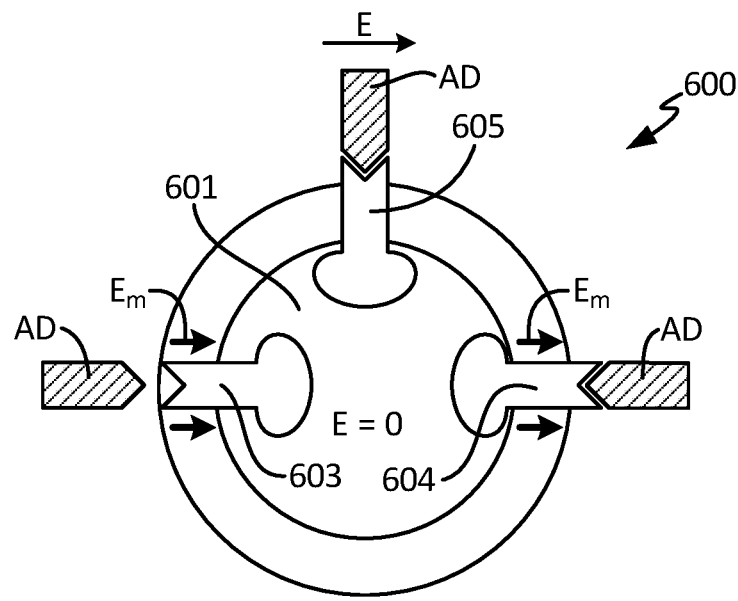
FIG. 6*b* is a diagram of the interaction of adenosine receptors with the electric field due to PEMF stimulation of the kidney according to an example embodiment where the cell is shown in electrical field E.
Figure 7:
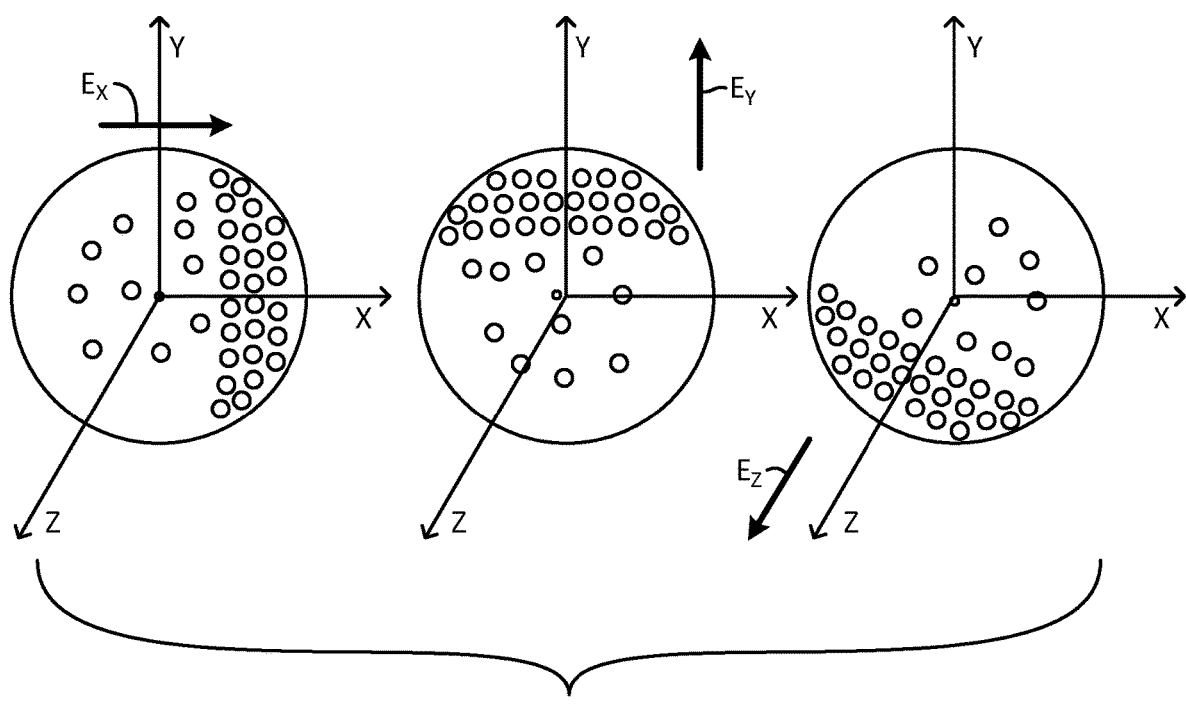
FIG. 7 is a series of diagrams illustrating application of stimulating Ex, Ey and Ez electric fields according to an example embodiment.

The stimulating electric field E is a vector. This fact and the consequences of the vector nature of the stimulating field have not been previously appreciated in the art. FIGS. 6a, 6b and 7 schematically illustrate the importance of this feature. Further discussion herein will be conducted with the assumption that the electric pulses applied to a cell are of appropriate amplitude and duration for activation of Ata receptors. This means that the applied electric pulses are about or higher than 1 mV/cm in amplitude and their duration is significantly longer than a time of cell relaxation, which is about 1 microsecond. In contrast, the durations conventionally used in the art are mainly in the range of 25-1000 microseconds.

At the beginning of each pulse, a transient period lasting about 1 microsecond takes place. During this period, the mobile ions inside the electrically conductive cytoplasm and the intercellular space outside the cell are redistributed in such a way that the electric field inside the cytoplasm is zero. After the transient period, the cell stays under stationary (static) distribution of the electric field during the rest of the pulse.

This redistribution of the ions leads to significant change of electric fields in the membrane. The maximums of electric field Em are located in the parts of membrane that is normal to the applied field and close to zero minimums where the membrane surface is parallel to external field E. The electric field Em in the membrane is defined by the ratio of the cell size to the thickness of membrane and is about 1000 times of the external electric field, comprising approximately 1000 mV/cm.

Because the actual electric field in membrane depends on the size of the cell, larger cells are more susceptive to the electric stimulation than smaller ones. For example, the linear size of macrophages is about 2.5 times the size of neutrophils, which means that activation of A2a receptors on macrophages is easier to achieve. And this is good news, because the major damage to kidney in CKD is done by the relatively large macrophage cells.

The process of interaction of adenosine receptors with the electric field is illustrated in FIGS. 6a and 6b. FIG. 6a represents a cell without electric field. For simplicity, only several receptors are shown; in reality, hundreds to thousands of A2a receptors are imbedded in a membrane of one cell. Numeral 601 designates cytosol, the inside volume of the cell separated from the intercellular space by a lipid membrane 602, the thickness of which is exaggerated for clarity of explanation. Numerals 603 and 604 designate adenosine A2a receptors, which are in the inactive state and are unable to bind with adenosine ligands and transduce biological signals into the cell. Adenosine ligands are depicted in FIGS. 6*a* and 6*b* as AD; they are present around the cell in significant concentration and are available for binding with active A2a receptors. Numeral 605 is an active A2a receptor bound to adenosine ligand.

FIG. 6*b* represents the same cell in electrical field E. In the membrane, maximal electric field Em is applied to receptors 603 and 604. This electric field is about 1000 times higher than applied field E and is capable of switching A2a receptors from the inactive to the active state (from OFF to ON).

The voltage sensor that switches cellular receptors is a two-position switch. It includes a charged group of atoms capable of moving from one position to another under action of electric field. Only one direction of the electric field parallel to the axis of its sensitivity can affect the position of the electric switch (voltage sensor) of the receptor and turn it ON. The opposite direction of the electric field can only push the charged group of atoms in the OFF position, where it already is, so no switching occurs. Assuming that the direction of switching ON is from inside the cell to outside, the switched ON receptor will be 604.

Relocation of the charged group of atoms in the receptor protein molecule causes its conformational change and makes the receptor capable of binding with adenosine ligands. Thus, receptor 604 becomes active, promptly binds with adenosine ligand AD from outside the cell and becomes a bound receptor that transduces the biological signal into the cell and farther along the adenosine signaling pathway.

As experimental data on PEMF activation of A2a receptors suggests, the total amount of A2a receptors activated by a one-dimensional electric field is approximately equal to the number of active receptors without electric stimulation. Thus, a one-dimensional electric stimulation causes a two-fold increase of adenosine active receptors, while three-dimensional stimulation causes a four-fold increase of active receptors or doubles the increase of the one-dimensional electric stimulation.

FIG. 7 schematically illustrates applications of stimulating Ex, Ey and Ez electric fields. An electric field applied along one axis, for example X, practically does not affect the electric field and receptors located in the plane normal to the applied field, YZ plane. The same is true for the other two axis, Y and Z. The receptors located in planes XZ and XY, respectively, are not sensitive to normal electric fields.

As shown in FIG. 7, sequential stimulation along each of axis X, Y and Z adds three new groups of activated receptors and leads to a four-fold increase of total numbers of active A2a receptors on a cell. These receptors additionally activated by stimulation and ligand bound A2a receptors are relatively stable; they disassociate with ligands and return to a basal state around 2 hours after the end of stimulation.

For simplicity in this disclosure, only unipolar electric pulses are discussed. However, stimulating pulses of the opposite polarity can be used as well. In such case, the pulsed electric field is applied in one direction for a period of time long enough to activate receptors and have them bind to the ligands; then the pulsed electric field of opposite direction is applied for the same period of time and the cycle is repeated. The electric field of the opposite direction cannot switch off the activating switch in a receptor that is already bound to a ligand, so activated and bound to ligands receptors will be accumulated on both ends of the stimulated cell along the direction of electric field.

The period of stimulation time in one direction can be about 5 to 15 minutes. Bipolar stimulation will activate even more A2a receptors and provide even stronger adenosine anti-inflammation and immune-suppressive signaling. For this bipolar embodiment, a simple circuit for reversing electric currents in coils is added to the apparatus. These types of reversing circuits are well known to those skilled in the art.

In a preferred embodiment of the invention, controller 109 provides DC pulses sequentially, one pulse at a time, to coils 209, 212 and 215, thereby creating electric fields along axes X, Y, Z. It is contemplated though, that pulses may be provided to two or three coils simultaneously with different relative amplitudes and polarities. This type of stimulation is more complicated, but allows for producing electric fields in any direction across the cell and can achieve the highest possible activation rate of the receptors A2a.

A2a adenosine receptors under applied electric field experience a conformational change that makes them able to bind with adenosine ligands. In an A2a protein molecule there is an electric field sensor comprising a charged group of atoms that operates as a switch creating this conformational transition. Whatever the nature of the electric field sensor is, under influence of electric field E, a charged group of atoms (ion) of the sensor is moving with a velocity Vi defined by the equation:

$$Vi = \mu E \quad (1)$$

Here constant µ is mobility of the ion.

During a stimulating electric pulse, the ion will travel distance ΔL equal to the product of velocity Vi and duration τp:

$$\Delta L = Vi\, \tau p = \mu E \tau p = \mu(E \tau p) \quad (2)$$

Thus, every stimulating pulse shifts the electric switch of a receptor on a distance ΔL equal to mobility of the ion µ multiplied by Eτp—the product of electric field and pulse duration. Value Eτp sometimes is called "electric impulse".

After accumulating multiple shifts, the switch relocates from the OFF position into the ON position and stays there. From the equation for ΔL, an important scaling law can be inferred: two different pulses produce the same stimulating effect if the product of their amplitudes and durations are the same. This scaling law, which was not appreciated in the previous art, is significant. It gives additional understanding and freedom in selecting durations and amplitudes of PEMF systems. In accordance with specific requirements of his system a designer can select higher electric field amplitudes in combination with shorter durations, or lower amplitudes with longer durations in wide range of values, and still have the same efficiency, provided their electric impulses are equal:

$$E\tau p = constant \quad (3)$$

Operation of the PEMF system will now be described. For simplicity, only one stimulating unit 200 will be described. The two stimulating two units (one for each kidney) can be connected to each other in parallel or in series, so their operations are essentially are identical.

The applicator belt 102 is positioned on the back of the patient around his/her waist. An operator turns on the system by push-button 111. Controller 109 starts generating DC electric pulses energizing in sequence stimulators 103 and 104. The pulses preferably are short, in tens to hundreds of microseconds, so the current through the coils never reaches the maximum that corresponds to the DC voltage. Exponentially growing currents in coils 209, 212 and 215 creates time varying magnetic fields that induce electric fields in the treatment area. Induced electric fields are circular; their lines are locked on themselves and lie in vertical or horizontal planes as shown in FIGS. 5*a*, 5*b* and 5*c*.

All coils of the apparatus have a respective free wheel diode connected in parallel to each coil. During a pulse, when a coil is connected to the DC power supply, a significant amount of energy delivered by the power supply is spent creating a magnetic field around the coil. At the end of a pulse, when the coil is cut off from the DC pulse, the magnetic energy induces an electric current in the circuit made by the coil and the companion free wheel diode connected in parallel to the coil. This redirection of magnetic energy into a coil-diode loop protects the circuits from high voltage spikes created by current interruptions in the coil.

PEMF stimulation is performed at a constant or variable repetition rate in the range of 5 to 100 Hz. With this rate, the heat deposit in coils is low, in the range of several Watts. It is not sufficient for successful thermal stimulation of the treatment area. Adequate thermal stimulation is achieved by using additional heater 201 placed adjacent to the treatment area and secured together with electromagnetic coils in one stimulating unit 200.

Temperature sensor 207 is placed on heater 201 to avoid overheating and to achieve better control of the treatment zone temperature. Controller 109 provides power to the heater 201 by delivering DC pulses with the same frequency (repetition rate) as the PEMF stimulation but, depending on the readings of temperature sensors, pulses with different durations. Actual power delivered to the heaters 201 is controlled by the duration of the pulses. When the temperature reading reaches the value higher or lower than predetermined by the controller, the pulse duration is shortened to allow the applicator to cool down or prolonged to heat it up and keep the temperature stable. The physiological feeling of comfortable warmth in the back may be used as an indication that the temperature is right and should not be increased or decreased. The temperature desired for successful thermal stimulation is about 42-43 degrees Celsius at the patient's skin. In another implementation of invention a sequence of short pulses is supplied by controller 109 to the heater 201 with numbers of heating pulses modulated by the temperature reading and a desired temperature setting.

FIG. 8 illustrates voltage (a), current and magnetic field (b), electric field (c) and thermal pulses (d and e) used in certain embodiments of the apparatus and kidney treatment method. When a DC step voltage $V_0$ is applied to an inductive coil of the stimulator, the electric current I and the magnetic field B generated by it grow exponentially.

At the beginning of a pulse, magnetic field B increases practically linearly (b). So, stimulating field E, which follows B as a derivative function, is almost constant (c). The DC pulse is interrupted by controller 109 with duration of pulse $\tau_p$ being 5-10 times shorter than the time of relaxation of the inductive circuit $\tau=L/R$, where the inductance of the coil is L and its resistance R.

In one embodiment of the present invention, the duration of DC pulses applied to the treatment coils is in the range of 5 µs to 100 µs. In another embodiment, the duration of pulses is in the range of 50 µs to 200 µs. In yet another embodiment, duration of pulses can be as high as 1000 µs.

The maximum magnetic field Bmax in the treatment zone in one embodiment is in the range of 0.5 mT to 1.0 mT. In another embodiment Bmax is in the range of 1.0 to 10.0 mT.

The maximum electric current through coils is 100-500 A.

The pulsing frequency (repetition rate) f used for PEMF stimulation and temperature control is in the range of 5 to 100 Hz.

In any case, whatever the Bmax and duration of the pulse τp is, the electric field E in the treatment zone should preferably stay in the range of 0.1 mV/cm to 20 mV/cm. A higher amplitude E with a shorter pulse duration τp or lower amplitude with longer pulse duration can be used, but their product Eτp, in accordance with the scaling law should be not less than a minimum value of about 100 µsmV/cm.

In the wide range of electrical field amplitudes E and durations τp described above, there is a rule for selection of the right combination of the amplitude and duration: 1000 µsmV/cm>=E τp>=100 µsmV/cm. Repetition rate f in the range of 5 Hz to 100 Hz produces the same biological effects and its choice is not significant for stimulation.

FIG. 8 graph d) illustrates voltage pulses sent by controller 109 to heater 201. The duration of pulses τh is modulated for stabilization of temperature at a desired level. In the case where a high frequency is used for heating of treatment zone, pulse τh depicts the heating power generated by HF generator.

FIG. 8 graph e) illustrates sequence of heating pulses when they are short and modulation of applied heat is done by changing their numbers.

In one example of treatment regimen for chronic kidney disease, separate sessions of deep heating with ultrasound or HF hypothermia heater or hot bath or sauna 3 to 4 times a week combined with PEMF treatment 3 to 7 times a week can be utilized.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

It is also within the scope of the invention to combine features, functions, advantages and aspects of the various embodiments described herein. Thus, the embodiments of the invention may comprise combinations of aspects of any one or more of these exemplary embodiments.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A method of treating chronic kidney disease of a mammal, the method comprising:
   increasing a concentration of Ata adenosine receptors on cellular membranes in a kidney of the mammal by:
   delivering a first pulsed magnetic field with a first polarity to the kidney of the mammal along a first orthogonal direction;
   delivering a second pulsed magnetic field with the first polarity to the kidney of the mammal along a second orthogonal direction, the second orthogonal direction being perpendicular to the first orthogonal direction, the first and second orthogonal directions being in a common plane; and
   delivering a third pulsed magnetic field with the first polarity to the kidney of the mammal along a third orthogonal direction, the third orthogonal direction being perpendicular to the common plane.

2. The method of claim 1, further comprising delivering each of the first pulsed magnetic field, the second pulsed magnetic field and the third pulsed magnetic field to the kidney of the mammal in a second polarity that is an opposite polarity compared to the first polarity.

3. The method of claim 1, further comprising:
applying a pulsed electromagnetic field (PEMF) treatment session to the kidney of the mammal on at least three days during a seven day period, wherein each PEMF treatment session lasts for two to four hours and includes delivering during the PEMF treatment session each of the first pulsed magnetic field, the second pulsed magnetic field and the third pulsed magnetic field to the kidney of the mammal; and
applying an independent whole body heat stimulation to the mammal two to four times during the seven day period to induce heat shock proteins in the kidney of the mammal.

4. The method of claim 1, further comprising heating the kidney of the mammal by energizing a high frequency generator.

5. The method of claim 1, further comprising generating a first electrical current in a first coil such that the first electrical current flows in a clockwise rotational direction in a first petal of the first coil and the first electrical current flows in a counter-clockwise rotational direction in a second petal of the first coil, wherein the first coil delivers the first pulsed magnetic field.

6. The method of claim 5, further comprising generating a second electrical current in a second coil such that the second electrical current flows in a clockwise rotational direction in a first petal of the second coil and the second electrical current flows in a counter-clockwise rotational direction in a second petal of the second coil, wherein the second coil delivers the second pulsed magnetic field.

7. The method of claim 1, further comprising energizing each of a first coil, a second coil and a third coil at a frequency of 1-1000 Hz to generate an electrical field that delivers a respective one of the first pulsed magnetic field, the second pulsed magnetic field and the third pulsed magnetic field.

8. The method of claim 1, further comprising energizing each of a first coil, a second coil and a third coil with an electrical impulse of not less 100 μsmV/cm to deliver a respective one of the first pulsed magnetic field, the second pulsed magnetic field and the third pulsed magnetic field.

9. The method of claim 1, further comprising:
delivering the first pulsed magnetic field via a first coil;
delivering the second pulsed magnetic field via a second coil;
delivering the third pulsed magnetic field via a third coil; and
arranging the first, second and third coils in a common plane.

10. The method of claim 9, further comprising arranging the first and second coils within a perimeter loop of the third coil.

11. The method of claim 10, further comprising forming each of the first and second coils such that the first coil resembles a first FIG. 8 and the second coil resembles a second FIG. 8.

12. The method of claim 9, further comprising forming each of the first and second coils such that the first coil resembles a first FIG. 8 and the second coil resembles a second FIG. 8.

13. The method of claim 1, further comprising providing heat input to the mammal sufficient to maintain a body surface temperature measurement in a range of 40-43 degree Celsius.

14. A method of treating chronic kidney disease of a mammal, the method comprising:
delivering by a first coil a first pulsed magnetic field to a kidney of the mammal;
delivering by a second coil a second pulsed magnetic field to the kidney of the mammal;
delivering by a third coil a third pulsed magnetic field to the kidney of the mammal;
arranging the first, second and third coils in a common plane; and
applying a treatment session to the kidney of the mammal on at least three days during a seven day period, wherein each treatment session lasts for two to four hours and includes delivering the first pulsed magnetic field, the second pulsed magnetic field and the third pulsed magnetic field to the kidney of the mammal.

15. The method of claim 14, further comprising arranging the first and second coils within a perimeter loop of the third coil.

16. The method of claim 14, further comprising configuring each of the first and second coils such that the first coil resembles a first FIG. 8 and the second coil resembles a second FIG. 8.

17. The method of claim 14, wherein each treatment session further includes applying heat input to the mammal sufficient to maintain a body surface temperature measurement in a range of 40-43 degree Celsius.

18. A method of treating chronic kidney disease of a mammal, the method comprising:
increasing a concentration of Ata adenosine receptors on cellular membranes in a kidney of the mammal by:
applying a pulsed electromagnetic field (PEMF) treatment session to the kidney of the mammal on at least three days during a seven day period, wherein each PEMF treatment session lasts for two to four hours and includes delivering a first pulsed magnetic field, a second pulsed magnetic field and a third pulsed magnetic field to the kidney of the mammal; and
applying an independent whole body heat stimulation to the mammal two to four times during the seven day period to induce heat shock proteins in the kidney of the mammal,
wherein the first pulsed magnetic field is delivered via a first coil,
wherein the second pulsed magnetic field is delivered via a second coil,
wherein the third pulsed magnetic field is delivered via a third coil, and
wherein each of the first, second and third coils are arranged in a common plane.

19. The method of claim 18, further comprising:
arranging the first and second coils within a perimeter loop of the third coil; and
orienting the second coil along an orthogonal axis that is ninety degrees offset from an orthogonal axis of the first coil.

* * * * *